US011395674B2

(12) United States Patent
Kelly

(10) Patent No.: US 11,395,674 B2
(45) Date of Patent: Jul. 26, 2022

(54) ROTARY DEBULKING ATHERECTOMY DEVICE WITH A CROSSING BALLOON

(71) Applicant: Cardinal Health Switzerland 515 Gmbh, Baar (CH)

(72) Inventor: William Kelly, Los Altos, CA (US)

(73) Assignee: Cardinal Health Switzerland 515 Gmbh, Baar (CH)

(*) Notice: Subject to any disclaimer, the term of this patent is extended or adjusted under 35 U.S.C. 154(b) by 66 days.

(21) Appl. No.: 16/470,029

(22) PCT Filed: Dec. 4, 2017

(86) PCT No.: PCT/EP2017/081412
§ 371 (c)(1),
(2) Date: Jun. 14, 2019

(87) PCT Pub. No.: WO2018/108607
PCT Pub. Date: Jun. 21, 2018

(65) Prior Publication Data
US 2020/0008835 A1 Jan. 9, 2020

Related U.S. Application Data

(60) Provisional application No. 62/435,309, filed on Dec. 16, 2016.

(51) Int. Cl.
*A61B 17/3207* (2006.01)
*A61B 17/00* (2006.01)
(Continued)

(52) U.S. Cl.
CPC .......... *A61B 17/320758* (2013.01); *A61B 2017/00336* (2013.01); *A61B 2017/22044* (2013.01);
(Continued)

(58) Field of Classification Search
CPC .. A61B 17/320758; A61B 2017/22044; A61B 2017/22054; A61B 2017/22071;
(Continued)

(56) References Cited

U.S. PATENT DOCUMENTS 5,250,060 A * 10/1993 Carbo ............ A61B 17/320725
604/164.13
6,126,635 A * 10/2000 Simpson ........ A61B 17/320758
604/101.05
(Continued)

FOREIGN PATENT DOCUMENTS

EP 2099368 9/2009
EP 2979722 2/2016

OTHER PUBLICATIONS

International Search Report and Written Opinion for International Application No. PCT/EP2017/081412; dated Jun. 21, 2018.

*Primary Examiner* — Robert A Lynch
(74) *Attorney, Agent, or Firm* — ArentFox Schiff LLP

(57) ABSTRACT

An atherectomy system that utilizes an anchoring balloon with a rotary debulker and a crossing balloon to remove or debulk lesions formed on the interior wall surface of a body vessel. The system may include a first balloon coupled to a first tubular member, a rotary debulker coupled to a second tubular member, a second balloon coupled to both the third tubular member and the axially moveable fourth tubular member such that the second balloon is disposed inside the third tubular member. Methods for operating this device are also provided.

2 Claims, 7 Drawing Sheets

(51) Int. Cl.
  *A61B 17/22* (2006.01)
  *A61B 17/34* (2006.01)
  *A61M 25/01* (2006.01)

(52) U.S. Cl.
  CPC .............. *A61B 2017/22054* (2013.01); *A61B 2017/22094* (2013.01); *A61B 2017/3435* (2013.01); *A61M 25/0119* (2013.01)

(58) Field of Classification Search
  CPC .. A61B 2017/22094; A61B 2017/3435; A61B 2017/320004; A61B 2017/320766; A61B 2017/320775; A61B 2017/00336; A61B 2017/22042; A61B 2017/22045; A61B 2017/22047; A61B 2017/22048; A61B 2017/22051; A61M 25/0199
  See application file for complete search history.

(56) References Cited

U.S. PATENT DOCUMENTS

| | | |
|---|---|---|
| 6,565,588 B1 | 5/2003 | Clement et al. |
| 7,674,272 B2 | 3/2010 | Torrance et al. |
| 8,377,037 B2 | 2/2013 | Sachdeva et al. |
| 2009/0099581 A1 | 4/2009 | Kim et al. |
| 2012/0302996 A1* | 11/2012 | Barash .............. A61M 25/0028 604/509 |
| 2014/0343593 A1* | 11/2014 | Chin ............... A61M 25/09041 606/194 |
| 2015/0051625 A1 | 2/2015 | Petrucci et al. |
| 2015/0142045 A1* | 5/2015 | Bacich ................. A61F 2/0027 606/193 |
| 2016/0354585 A1* | 12/2016 | Pigott ................... A61M 25/10 |

\* cited by examiner

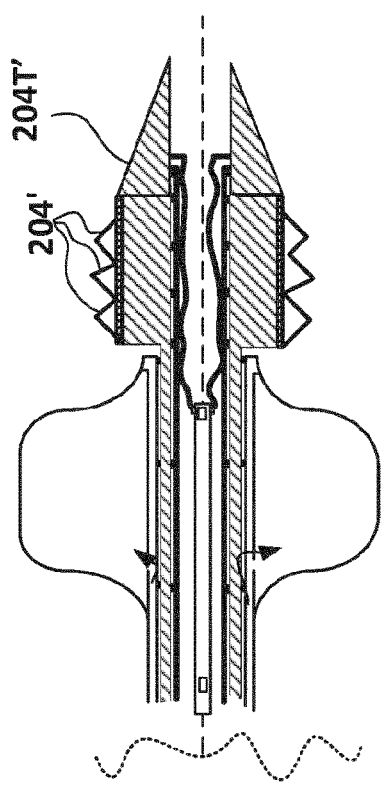
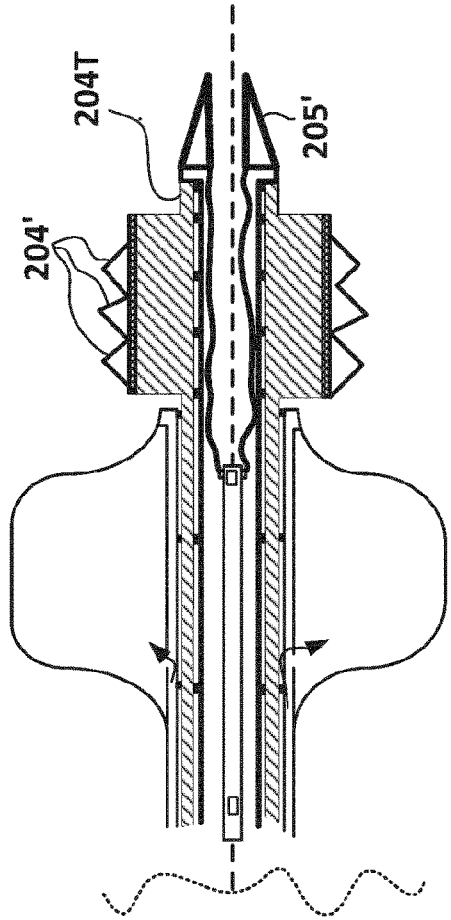
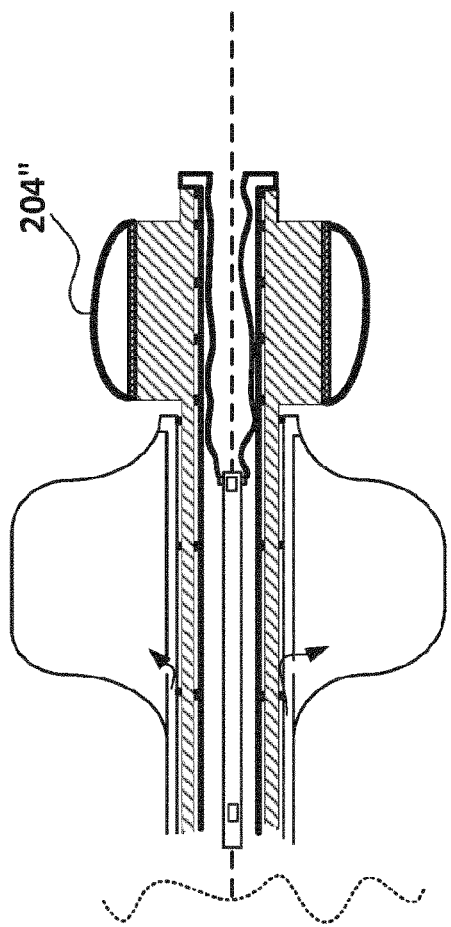

ROTARY DEBULKING ATHERECTOMY DEVICE WITH A CROSSING BALLOON

PRIORITY

This application claims the benefits of priority under the Paris Convention as well as 35 USC § 119 to U.S. Provisional Patent Application Ser. No. 62/435,309 filed on Dec. 16, 2016, of which the entirety of the prior application is incorporated by reference herein.

BACKGROUND

For certain arterial diseases (e.g., peripheral arteries including the iliac, femoral, popliteal and tibial arteries) where plaques have built up onto the internal surface of blood vessel walls or thrombus in some cases (i.e., arterial occlusive disease), it is known to use a variety of techniques to improve blood flow through these vessels including, for example, angioplasty, stents or atherectomy. Angioplasty or stenting is believed to be ineffective when plaques may include irregular, loose or calcified deposits as these techniques simply compress the plaques further into the blood vessel walls with the attendant risk of vascular injuries. Atherectomy, on the other hand, where the plaque is physically removed, is believed to be more effective for calcified, fibrotic, as well as soft or longer lesions or lesions involving side branches in the peripheral arteries. The benefit of atherectomy is believed to arise from a reduction of plaque burden on the arterial wall that apparently does not affect the rest of the vessel walls post treatment.

Currently, several atherectomy devices are available on the market with FDA approval. These devices are categorized as laser ablation, orbital, rotational or directional atherectomy devices. Examples of such devices are described in U.S. Pat. Nos. 6,565,588; 7,674,272; 8,377,037; and "Atherectomy in the Treatment of Lower-Extremity Peripheral Artery Disease: A Critical Review" by Girish R. Mood, MD, Juyong Lee, MD, PhD, Lawrence A. Garcia, MD; St. Elizabeth's Medical Center, Tufts University School of Medicine, Division of Interventional Cardiology and Vascular Medicine, Boston, Mass. (2013).

One shortcoming of these devices is the need to cross a lesion that is so occlusive to the body vessel that a working tip of the devices cannot act on. For example, where the plaque removal device has an outer diameter larger than the inside diameter of the plaque occlusion, the plaque removal device may not be able to apply its debulking action against the plaque. In such a situation, the typical mitigation is to remove the debulking tip, changing to a different tip that can act as a drill to cross the lesion. Using the drill-like tip may cause dissection of the vessel leading to further complications for the patient. Another mitigation technique is to use a crossing balloon but this inefficient and may cause trauma by overcompression of the lesion as well as the dispersion of unwanted emboli in the body vessel.

SUMMARY OF THE DISCLOSURE

Recognizing these shortcomings of the aforementioned prior art, I have devised a heretofore new device that overcome these shortcomings. In particular, I have devised an atherectomy device that may include a handle and a working tip. The handle may include a housing that extends from a first housing end to a second housing end along a housing longitudinal axis with the first housing end being coupled to a first tubular member so that the first tubular member is coupled to the handle. The first tubular member surrounds at least a portion of a second tubular member. The second tubular member is coupled to a rotary member proximate the housing and disposed around a portion of a third tubular member. The third tubular member is disposed around a portion of an axially moveable fourth tubular member. The working tip is spaced from the handle and extends along a working tip longitudinal axis. The working tip may include a first balloon coupled to the first tubular member, a rotary debulker coupled to the second tubular member, and a second balloon coupled to both the third tubular member and the axially moveable fourth tubular member such that the second balloon is disposed inside the third tubular member.

In yet another embodiment, I have devised an atherectomy tip that may include an outer sheath, a first balloon, a rotary debulker, and a second balloon. The outer sheath extends along a longitudinal axis and surrounds a portion of a first tubular member. The first tubular member surrounds at least a portion of a second tubular member. The second tubular member is disposed around a portion of a third tubular member. The third tubular member is disposed around a portion of an axially moveable fourth tubular member. The first balloon is coupled to the first tubular member. The rotary debulker is coupled to the second tubular member so that the rotary debulker is rotatable about the longitudinal axis by rotational motion of the second tubular member about the longitudinal axis. The second balloon is coupled to both the third tubular member and the axially moveable fourth tubular member such that the second balloon is disposed partly inside the third tubular member.

In another embodiment, I have provided an atherectomy tip that may include an outer sheath covering a portion of a first, second, third and fourth tubular members. The outer sheath extends along a longitudinal axis and surrounds a portion of a first tubular member. The first tubular member surrounds at least a portion of a second tubular member, with the second tubular member being disposed around a portion of a third tubular member. The third tubular member is disposed around a portion of an axially moveable fourth tubular member. A first balloon is coupled to the first tubular member. A rotary debulker is coupled to the second tubular member so that the rotary debulker is rotatable about the longitudinal axis by rotational motion of the second tubular member about the longitudinal axis. A second balloon is coupled to both the third tubular member and the axially moveable fourth tubular member such that the second balloon is disposed partly inside the third tubular member.

In yet a further embodiment, I have devised method of debulking lesions disposed inside a body vessel with a catheter that may include an outer sheath extending along a longitudinal axis, the outer sheath surrounding a portion of a first tubular member, the first tubular member surrounding at least a portion of a second tubular member, the second tubular member disposed around a portion of a third tubular member, the third tubular member disposed around a portion of an axially moveable fourth tubular member; a first balloon coupled to the first tubular member; a rotary debulker being coupled to the second tubular member so that the rotary debulker is rotatable about the longitudinal axis by rotational motion of the second tubular member about the longitudinal axis; and a second balloon coupled to both the third tubular member and the axially moveable fourth tubular member such that the second balloon is disposed inside the third tubular member. The method can be achieved by inserting a catheter into the body vessel proximate the lesion; inflating the first balloon for abutment against the internal surface of the body vessel; rotating the rotary debulker to remove portions of the lesion at a first location; axially advancing the catheter into the lesion at a second location spaced from the first location; and pulling the fourth tubular member along the longitudinal axis in a distal direction by inflation of the second balloon so that a tip of the fourth tubular member extends into a plaque material occluding the vessel.

The method can further be utilized with the following steps, advancing the fourth tubular member along the longitudinal axis to dispose the second balloon outside of the third tubular member; inflating the second balloon to expand against the lesion; deflating the second balloon; deflating the first balloon; and rotating the rotary debulker to remove portions of the lesion.

Alternative embodiments of the invention can be achieved when utilized with other features noted hereafter with the embodiments referenced earlier. For example, the outer sheath comprises a polymeric tubular member having a proximal end mounted to the handle and configured for axial movement along the housing longitudinal axis so that when the outer sheath is moved axially in a proximal direction, a distal end of the outer sheath is moved axially in the proximal direction to uncover the first tubular member; the outer sheath further comprises a locking mechanism to prevent axial movement of the outer sheath; the first tubular member comprises a first polymeric member defining a first fluid passage that extends from a first fluid port disposed proximate the handle to an inner volume of the first balloon; wherein the second tubular member is supported for rotation relative to the first tubular member; wherein the second tubular member is supported for rotation relative to the third tubular member; wherein the third tubular member comprises a second polymeric member defining a second fluid passage in which the fourth tubular member is disposed in the second fluid passage; wherein the fourth tubular member is supported for axial movement along the working tip longitudinal axis; wherein the fourth tubular member is connected at a first terminal end of the second balloon and the third tubular member is connected to a second terminal end of the second balloon; wherein the fourth tubular member defines a guidewire passage for deployment of a guidewire; wherein the first balloon comprises a first outer diameter greater than a second outer diameter of the second balloon; wherein a maximum outer diameter of the rotary debulker is less than the first outer diameter of the first balloon.

These and other embodiments, features and advantages will become apparent to those skilled in the art when taken with reference to the following more detailed description of the exemplary embodiments of the invention in conjunction with the accompanying drawings that are first briefly described.

BRIEF DESCRIPTION OF DRAWINGS

The accompanying drawings, which are incorporated herein and constitute part of this specification, illustrate presently preferred embodiments of the invention, and, together with the general description given above and the detailed description given below, serve to explain features of the invention wherein like numerals represent like elements, in which:

FIG. 5A illustrates (not to scale) a cross-sectional view of an alternative embodiment of the distal end of the system in FIG. 2 with the debulker having teeth-like cutters;

FIG. 5B illustrates, again not to scale, a sectional view of yet another alternate debulker that uses wire-like members to cut through lesion P; and FIG. 5C illustrates, not to scale, a sectional view of another debulker configuration having an angled profile for ease of entry into a lesion.

MODES OF CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the root terms "distal" or "proximal" are referenced in relation to a user in which "distal" indicates that certain parts or components are further away to the user and "proximal" indicates that certain parts or components are closer to the user. It is noted that the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

The following description provides specific details for a thorough understanding of, and enabling description for, embodiments of the invention. However, one skilled in the art will understand that the invention may be practiced without these details. In other instances, well-known structures and functions have not been shown or described in detail to avoid unnecessarily obscuring the description of the embodiments of the invention.

Figure 1:
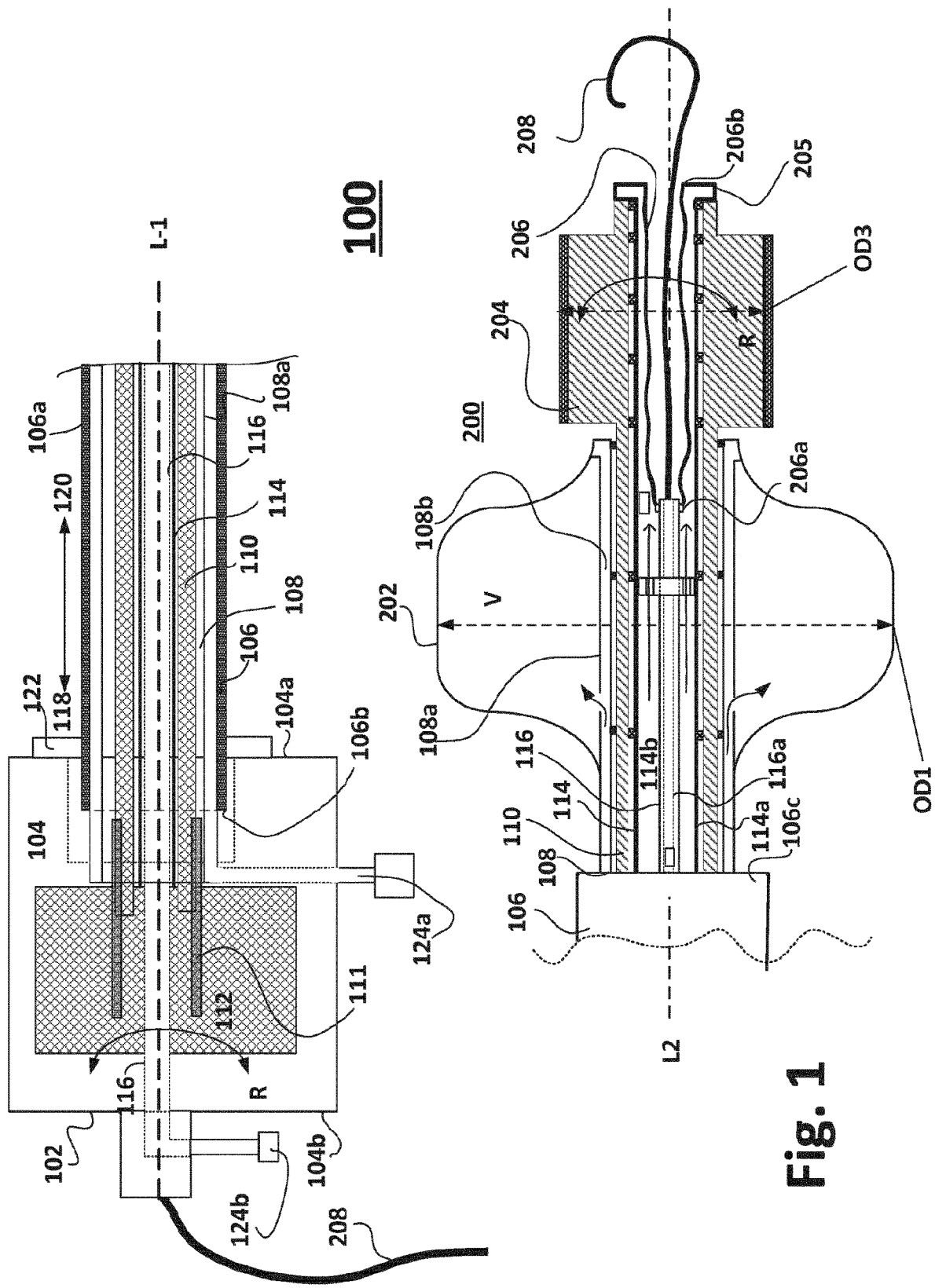
FIG. 1 illustrates a plan view of one embodiment of the catheter system 100.

Referring now to the figures wherein like numerals indicate the same element throughout the views, there is shown in FIG. 1 an atherectomy catheter system 100. The system 100 includes a handle 102, which is shown schematically as a housing 104 that extends from a first housing end 104a to a second housing end 104b along a housing longitudinal axis L1 towards a working end 200. The handle 104 is preferably ergonomic in design and sized to be gripped by one hand.

As shown, the first housing end 104a is coupled to an outer sheath 106 that extends from the handle 102 to a working tip portion 200. At the working tip portion 200, the outer sheath 106 is configured so that the sheath 106 surrounds a portion 108a of a first tubular member 108 and the first tubular member 108 is coupled to the handle 102. It should be noted here that the first tubular member 108 surrounds at least a portion of a second tubular member 110 with the second tubular member 110 being coupled to a rotary member 112 proximate the housing and disposed around a portion of a third tubular member 114. The third tubular member 114 is disposed around a portion of an axially moveable fourth tubular member 116. By virtue of the arrangement of five generally coaxial (or alternatively concentric) tubular members (i.e., outer sheath and first through fourth tubular members), a crossing balloon can be employed with a rotary debulker without sacrificing the performance of the debulker. It is noted that the outer sheath 106 can be made from a suitable biocompatible material, such as a polymeric material (e.g., PEEK, PEBAK, Nylon etc.,) for tubular member 106a. Alternatively, tubular member 106a can be in the form of a braided member with a suitable liner material.

The tubular member 106a has a proximal end 106b mounted to the handle 102 and configured for axial movement 118, 120 of the proximal end 106b along the housing longitudinal axis L1 so that when the outer sheath 106 is moved axially in a proximal direction 118 such as when the operator grips the outer sheath 106 to move the sheath 106, the distal end 106c of the outer sheath 106 is moved axially in the proximal direction 118 to uncover the first tubular member 108 at the working tip portion 200. To prevent or mitigate unintended unsheathing of the components at the working tip portion 200, the outer sheath 106 can be provided with a locking mechanism 122 to prevent axial movement of the outer sheath 106. Similar to the outer sheath 106, the first tubular member 108 can also be provided with a first polymeric member 108a that defines a first fluid passage 108b extending from a first fluid port 124a disposed proximate the handle 102 to an inner volume V of the first balloon 202. Continuing radially inward towards the longitudinal axis L1, the second tubular member 110 is supported for rotation relative to the first tubular member 108 while the second tubular member 110 is supported for rotation relative to the third tubular member 114. Moving further toward the axis L1, it can be seen that the third tubular member 114 can be provided as a second polymeric member 114a that has a second fluid passage 114b in which the fourth tubular member 116 is disposed in the second fluid passage 114b and the fourth tubular member 116 is supported for axial movement along the axis L1 or at the working tip portion 200, along working tip longitudinal axis L2. The fourth tubular member 116 can be configured to provide a passage 116a for deployment of a guidewire 208. As well, passage 116a can also be utilized as an aspirator (FIG. 2A) for removal of debris or emboli 300 during operation of the rotary debulker 204. While the drawings show a passage 116a in the form of a guidewire passage, it is noted that this invention does not require a guidewire for its intended operation.

As used herein, the term "proximal" denotes the location of the subject component closer to the operator whereas the term "distal" denotes the location of the subject component further away to the operator.

As shown in FIG. 1, the working tip 200 is configured to extend away from an operator (not shown) at a suitable distance (e.g., approximately 50-300 cm) from the handle 102 so as to allow for entry into an appropriate vascular access site (e.g., femoral, jugular or even radial artery). The working tip 200 extends along a working tip longitudinal axis L2 and includes a first balloon 202 coupled to the first tubular member 108 while a rotary debulker 204 is coupled to the second tubular member 110 with a second balloon 206 coupled to both the third tubular member 114 and the axially moveable fourth tubular member 116 such that the second balloon 206 is disposed inside the third tubular member 114. In particular, an outer sheath 106 may surround a portion 108a of a first tubular member 108 and the first tubular member 108 itself surrounds at least a portion of a second tubular member 110. At the working end 200, the first balloon 202 is coupled to the first tubular member 108 while the second tubular member 110 is disposed around a portion of a third tubular member 114. The third tubular member 114 itself is disposed around a portion of an axially moveable fourth tubular member 116. For debulking or breaking up of plaques in the artery, a rotary debulker is 204 is coupled to the second tubular member 110. In a preferred embodiment, the debulker 204 can be in the form of a sanding drum with various surface roughness configured therein to remove different forms of plaque. In this embodiment, the rotary debulker 204 is rotatable in a rotational direction R (e.g., clockwise or counterclockwise) about the longitudinal axis L2 by rotational motion of the second tubular member 110 about the longitudinal axis L2. The second tubular member 110 can be rotated by a rotary source 112 in the form of an electric motor or a pneumatic rotary motor. The debulker 204 is coupled via the second tubular member 110 to the rotary source 112 through a spline coupling 111. The spline coupling 111 allows the rotary source 110 to rotate the debulker 204 while also allowing the debulker 204 to translate along the longitudinal axis L1 due to the debulker 204 being connected to the tubular member 110.

The second balloon 206 is coupled to both the third tubular member 114 and the axially moveable fourth tubular member 116 such that the second balloon 206 is disposed partly inside the third tubular member 114.

In an alternative embodiment, outer sheath 106 can be eliminated to allow for a smaller outer profile (e.g., 5 French or smaller). In such an embodiment, the first tubular member 108 can function as an outer sheath with the balloon 202 mounted or wrapped around the first tubular member 108 in a fully deflated state.

It should be noted that the fourth tubular member 116 is connected at a first terminal end 206a of the second balloon 206 and the third tubular member 114 is connected to a second terminal end 206b of the second balloon 206. The first balloon 202 may have a first outer diameter OD1 greater than a second outer diameter OD2 of the second balloon 206. Note that a maximum outer diameter OD3 of the rotary debulker is less than the first outer diameter OD1 of the first balloon 202. Although the tip 205 is shown in FIG. 1A with a somewhat blunt configuration, other tip configuration can be provided, such as, for example, an atraumatic tip 205' in FIG. 5A.

Figure 2A:
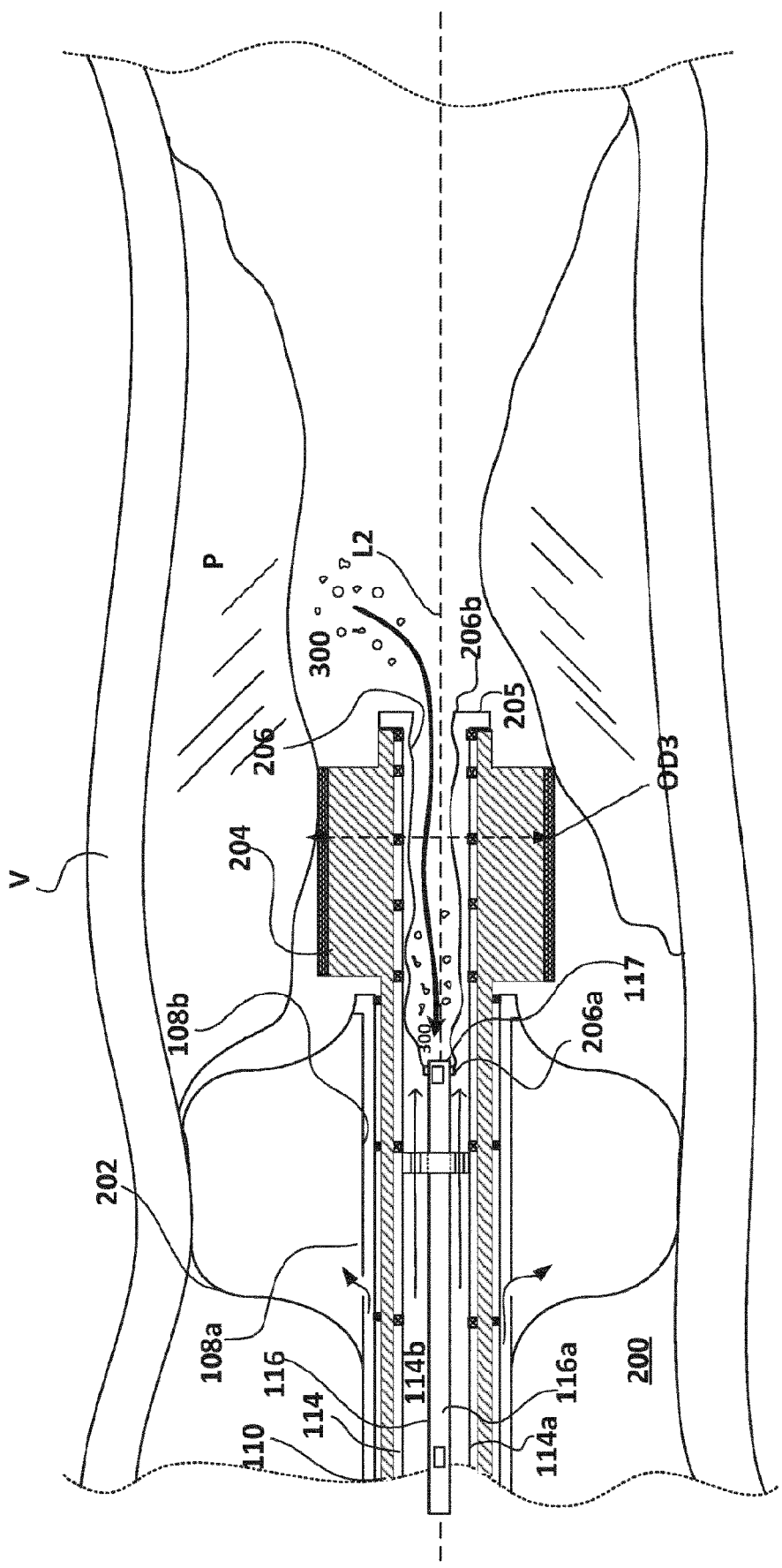
FIG. 2A illustrates a close up sectional view of the distal end of the system in FIG. 1 as diagrammatically represented inside a body vessel.

With reference to FIGS. 2A, 2B, 3, and 4, the operation of an exemplary embodiment is described. In FIG. 2A, it is assumed that the operator (e.g., healthcare provider) has gained entry of the working tip 200 adjacent to a plaque P inside the vessel V. At this point, the operator would inflate the first balloon 202 via passage 108b with saline (or a suitable biocompatible fluid). This allows the working tip 200 to be stabilized against the vessel so that any further distal movement of the tip 205 will have little or no pushback in the proximal direction. As well, the inflated first balloon 202 will allow the debulker 204 to cut through the lesion P cleanly with little or no whipping of the tip 205.

Figure 2B:
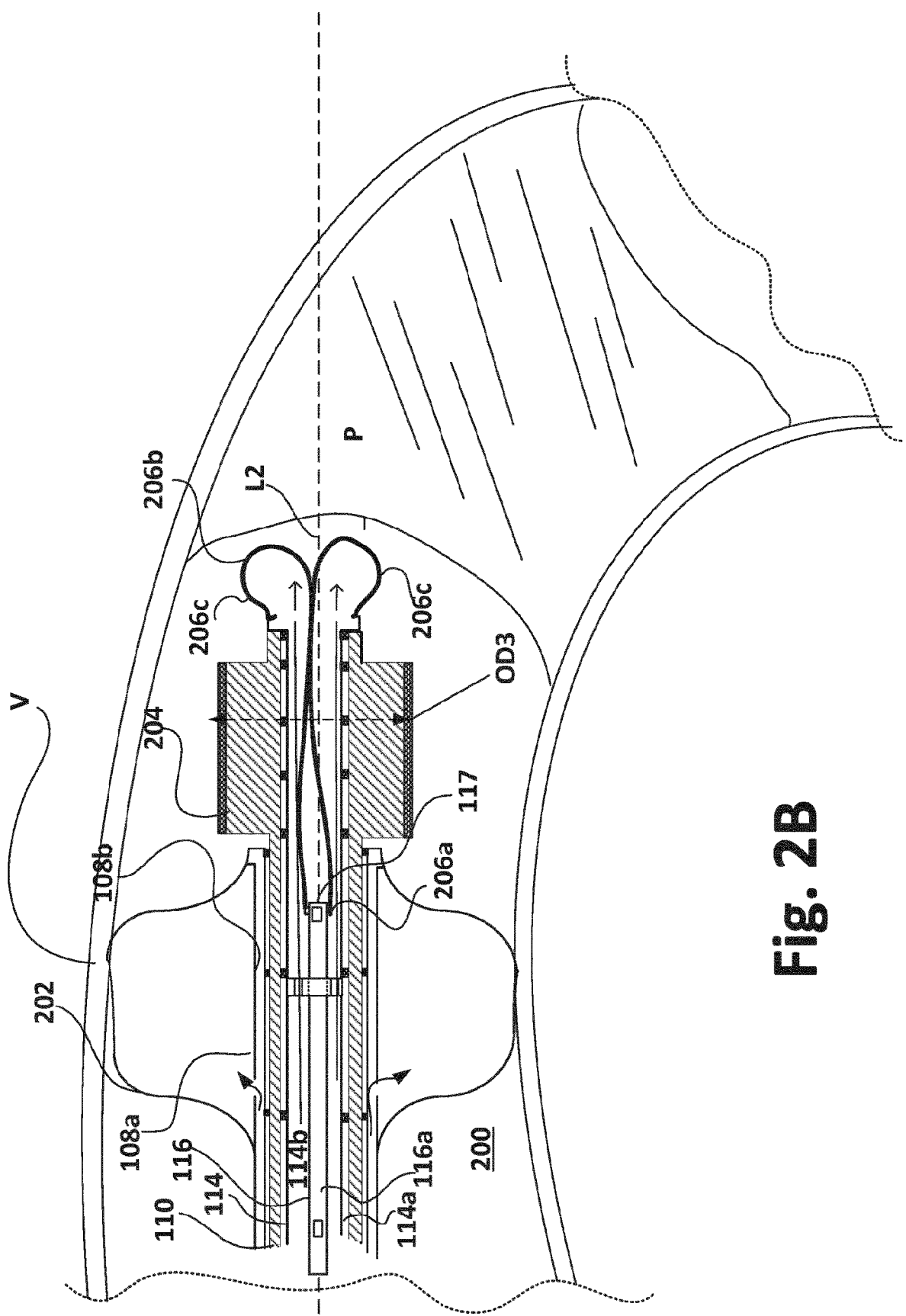
FIG. 2B illustrates a close up sectional view of the distal end of the system in a curved or tortuous vessel occluded by plaque.
Figure 2C:
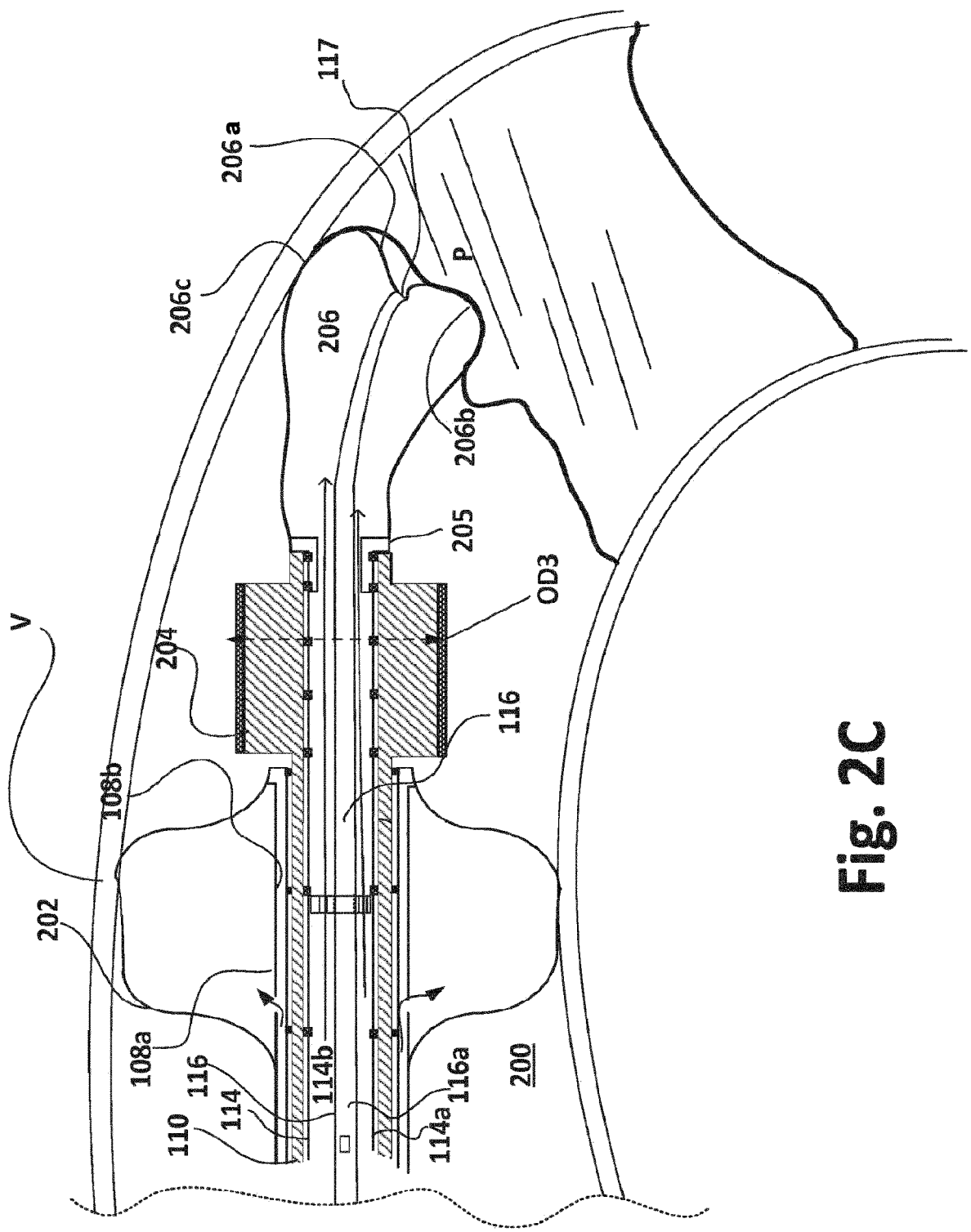
FIG. 2C illustrates the tip 117 of catheter 116 being "pulled" out of third tubular member 114 so as to extend into (i.e., "crossing") the lesion P.

Under certain conditions, plaques can be formed around a curved or tortuous portions of the body vessel, shown here in FIG. 2B. In such instances, a typical procedure to cross lesion P is to push the guidewire tip or a guidewire of the typical atherectomy device into the lesion. Due to the curved nature of the body vessel, shown exemplarily in FIG. 2B, it may be the case that the pushing of tip 116 may cause a dissection of the body vessel due to impingement of the distal tip of the atherectomy device on the vessel wall V. This shortfall of the typical atherectomy device is overcome by virtue of the principles of the invention as described and illustrated herein. Specifically, in-lieu of the operator pushing on the guidewire catheter (or fourth tubular member) 116 to cross the lesion P, the operator would inflate balloon 206 (via port 124a in FIG. 1). The inflation of balloon 206 causes an eversion or evaginating of the balloon 206 into a globular configuration 206c that protrudes into a distal tip portion 206b. As the balloon 206 is inflated to form the globule 206c, balloon 206 necessarily shortens, thereby pulling fourth tubular member 116 in a distal direction until the balloon is fully inflated, shown here in FIG. 2C and FIG. 3. This results in two benefits for the patient (as well as the operator): (1) the operator does not need to push on catheter 116 to cross the lesion P as the act of inflating balloon 206 will cause the outermost distal extension of the balloon 206a to be continued to be extended into the lesion; and (2) the globular like configuration 206c acts as a cushion for the vessel V as the distal extension of the balloon (i.e., its tip) crosses the lesion thereby preventing dissection of the vessel V. When the balloon 206 is fully inflated, the balloon distalmost tip 206b extends through the lesion P thereby "crossing the lesion" as is known in the art.

Figure 3:
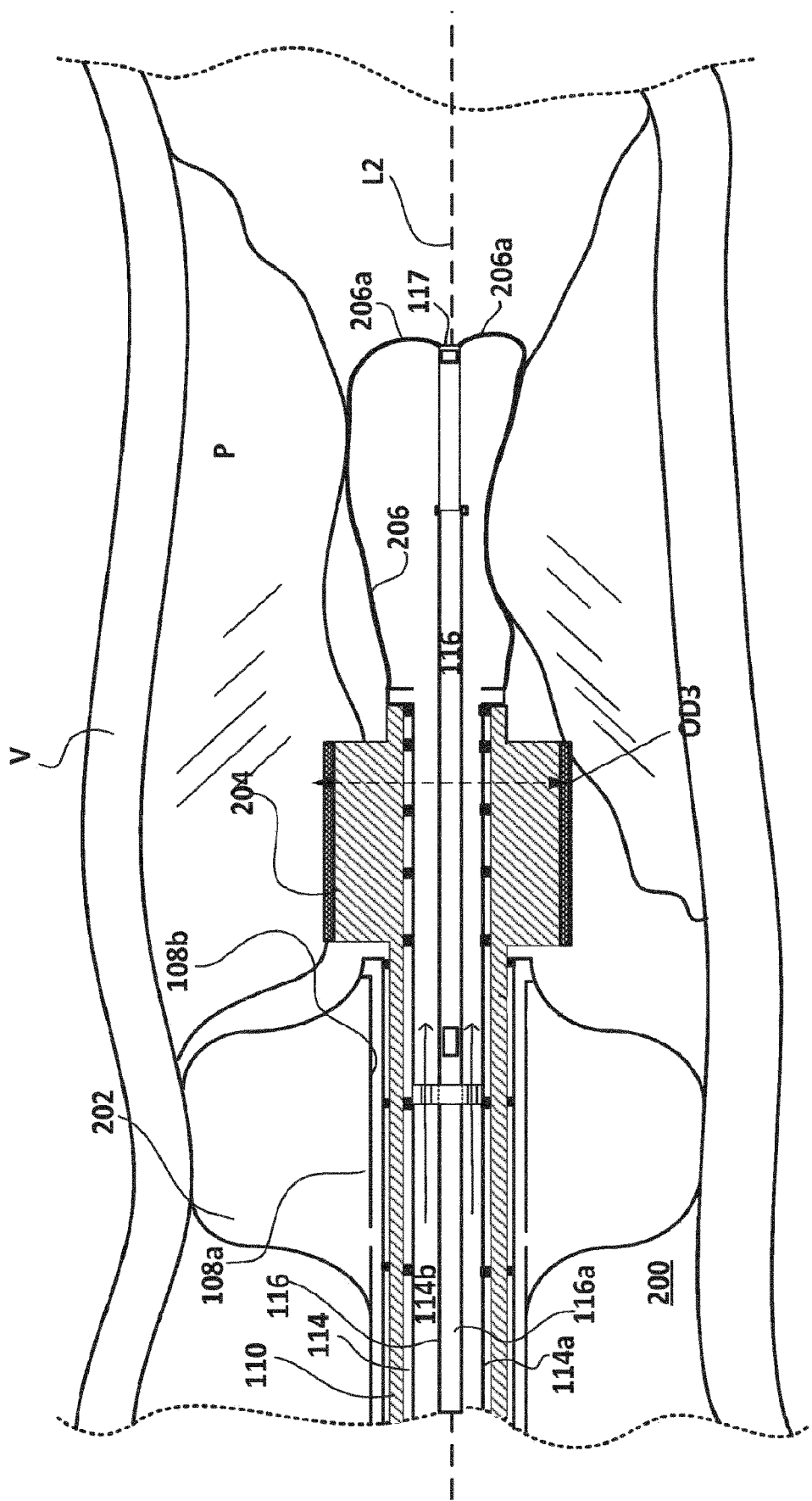
FIG. 3 illustrates (not to scale) a cross-sectional view of the distal end of the system in FIG. 2 as shown being advanced in the body vessel with the second balloon partially extended.

As seen in FIG. 3, there can be instances where the plaque P may be so calcified that it can be very difficult for the debulker 204 to cut through. In other instances, the plaque P may be so extensive that the debulker 204 cannot progress further into the lesion. At this point, the operator can utilize the second balloon to cross the lesion P by using inflation port 124a to introduce saline (or a suitable biocompatible fluid) under pressure to the space between tubular members 114 and 166 so as to inflate the balloon 206. Again, the crossing can be done by inflating the balloon 206 (which pulls the fourth tubular member 116 in the distal direction) as the balloon 206 is everted or invaginated from its location defined by the third tubular member 114. As the fourth member 116 is pulled distally by the inflating balloon 206, the first terminal end 206a is extended past the second terminal end 206b of the second balloon 206.

Figure 4:
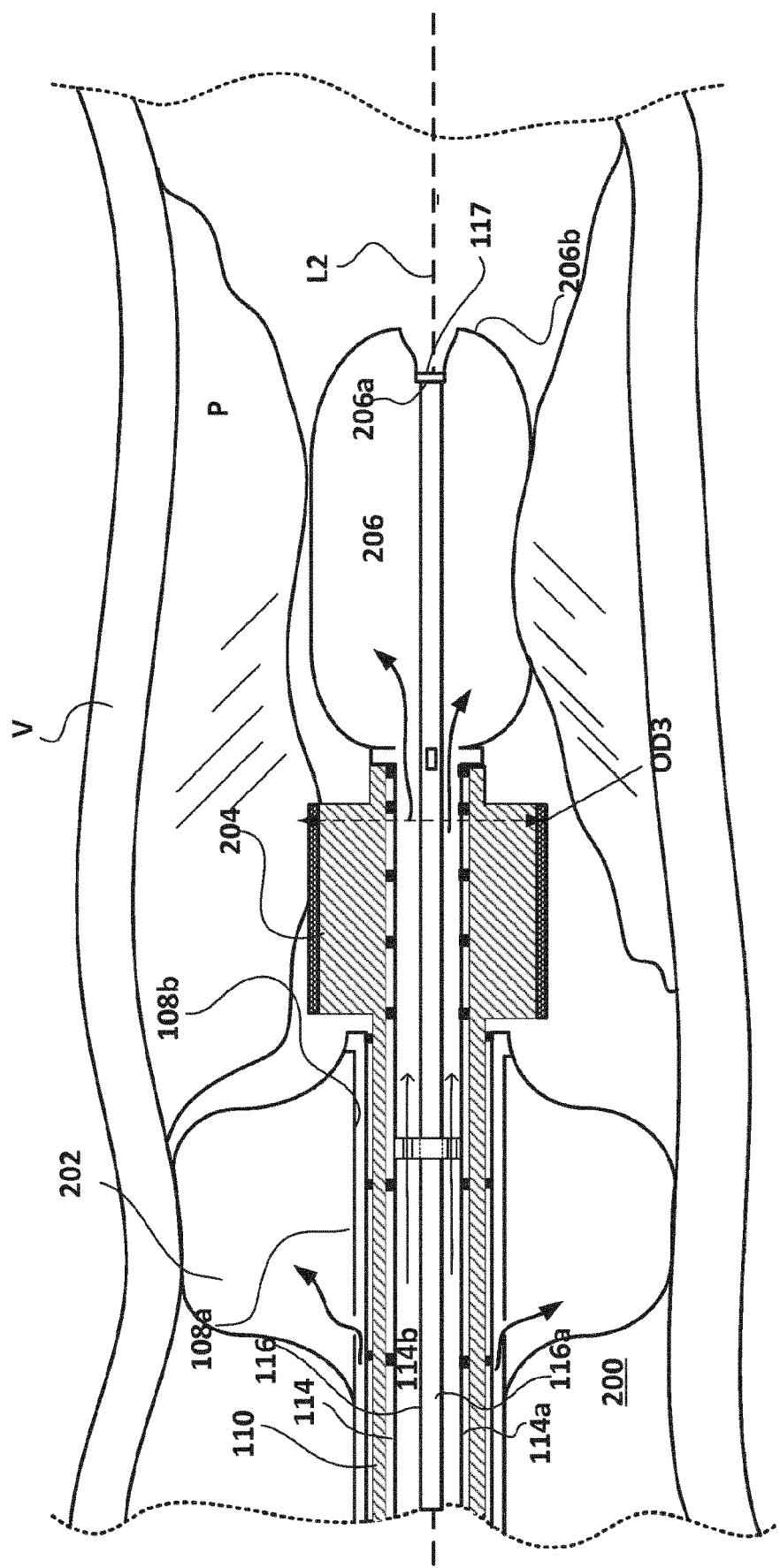
FIG. 4 illustrates, again not to scale, an end view of the distal end of the system in FIG. 3 with second balloon inflated.

As shown in FIG. 4, the second balloon 206 (also indicated as a crossing balloon as it "crosses" the lesion P) can be inflated via inflation port 124b with saline (or a suitable fluid) into the volume or space between third tubular member 114 and fourth tubular member 116 so that the lesion P can be compressed into the vessel V. This compression of the plaque P allows sufficient clearance for the debulker 204 to advance into the lesion and debulk portions of the plaque P and ultimately for the working tip 200 to traverse across the plaque as well as increasing the opening within the vessel V.

While the debulker 204 is shown in the form of a rotary drum, other configuration can also be provided. For example, debulker in the form of jagged surfaces 204' in FIG. 5A can be used to aggressive cut through the plaque. Alternatively, debulker in the form of steel wires 204" in FIG. 5B can be used to slice through the plaque in a manner akin to a garroting of the plaque. Because the steel wires 204" can extend its effective diameter via increased rotational speed, this embodiment has the benefit of reducing the amount of compression that is needed by the crossing balloon 206. Instead of a squared-off tip 204T in FIG. 5A, debulker 204 may have its tip 204T' configured in the form of an angled or pointed profile to allow for penetration of the lesion. Other outer profiles of the debulker 204 can be utilized such as, for example, conical or football shaped so as to fit into areas where balloon 206 does not fully expand when inflated.

As shown by the example above in relation to FIGS. 2-5, it can be seen now that I have devised a general method of debulking lesions or plaques in a vessel with two balloons and a debulker. Briefly, the first balloon acts as an anchor as well as preventing unwanted debris flowing in the proximal direction. The second balloon operates to pull guidewire tip 117 (instead of the operator pushing on the catheter 116 to push on tip 117). Once the balloon tip 206b has started to cross the plaque or occlusion P, the balloon 206 operates to further compress the lesion P so as to allow the rotary debulker 204 to perform its function in widening the flow area through the lesion. As the balloon 206 is further inflated, it operates to pull tip 117 along in the distal direction while maintaining the tip 117 enfolded inside the outermost perimeter of balloon 206. The benefit of this configuration is that the tip 117 is prevented from extending straight into the inner wall surface of the vessel V, thereby dissecting the vessel V when the catheter is crossing a tortuous or curved vessel V such as in FIG. 2C. In FIG. 2C, it can be seen that the fourth tubular member 116 is forced to conform along the curvature of the vessel due to the everting balloon 206 conforming its outer surface 206c to the inner curved wall surface of the vessel V while at the same time causing the tip 117 to be protected within the folds of the balloon 206, thereby preventing the tip 117 from dissecting the vessel wall V. Another advantage of this invention is that it allows for one product that streamlines the procedure by both debulking the plaque as well as crossing the plaque, thereby allowing for a higher level of efficiency and control during the procedure.

The crossing balloon 206 devised here is of a diameter that is smaller than the vessel internal diameter to prevent damage to the vessel walls when advancing through a total occlusion or heavily calcified occlusion. Over inflation of typical crossing balloons can cause tearing or damage to the vessel walls which would impede healing and cause increase risks of future stenosis. When the crossing balloon 206 is inflated it will provide more axial force than can be applied to a guide wire by hand, which will advance into the lesion, even through a total occlusion of the vessel V. The crossing balloon 206 is preferably smaller in diameter as compared to the first balloon 202 in order to keep the smaller diameter balloon 206 more on center with axis L2. Additionally, the balloon 206 can be of a suitable length to ensure that tip 117 of catheter member 116 can cross through a lesion as the balloon 206 is inflated to pull the tip 117 out of the third tubular member 114 as the tip 117 follows the balloon tip portion 206b in crossing the lesion P.

Specifically, this method can be performed with the following steps: inserting a catheter 100 (similar to that shown in FIG. 1) into a body vessel V (e.g., artery or vein) proximate a lesion P. Once the working tip 200 is at the appropriate position in relation to the plaque, usually by the tip abutting against the plaque. Once substantial resistant is felt in the handle, the operator would restrain the catheter from movement in the proximal movement by inflating the first balloon 202 for abutment against the internal surface of the body vessel. After the catheter is sufficient is fixed to the artery, the operator can activate the motor 112 (e.g., electric or pneumatic) which rotates third tubular member 114, thereby rotating the rotary debulker 204 to remove portions of the lesion P at a first location. While rotating the debulker 204, the debulker 204 can be advanced axially along axis L2 via the spline coupling 111 (FIG. 1) and tubular member 110. Alternatively, the entire assembly (member 114, debulker 204, member 116) can be axially advance in the distal direction along axis L2 to further remove plaque material by inflation of balloon 206 to pull tip 117 in the distal direction. The passage 116a (inside of fourth tubular member 116) can be utilized to aspirate debris or emboli 300 through port 124a (FIG. 1) to an external container (not shown). Once substantial resistance is felt by the operator at the handle or where the debulker 204 is fully extended, the operator can assist the debulker 204 in crossing the lesion by inflating the second balloon 206 to extend the balloon distal tip 206b into the lesion as well as pulling the tip 117 of catheter tube 116 out of third tubular member 114 as the balloon 206 is fully inflated. While the balloon tip 206b is preferably the leading member through the lesion to prevent dissection of the vessel by tip 117 (FIG. 4), it is also contemplated that in certain embodiments, tip 117 can be configured to be the leading member rather than that of the balloon tip 206b. Note that the second balloon 206 can be configured to have an outside maximum diameter greater than that of the debulker 204. For the preferred embodiment and to reduce any trauma to the native vessel V, the maximum outside diameter of the second balloon is approximately the same as that of the maximum outside diameter of the debulker 204.

After crossing of the balloon tip 206b (or tip 117) as well as compression of the plaque by the second balloon 206 to allow passage of the debulker, the operator deflates the second balloon 206 and continues rotation of the rotary debulker 204 (as well as axial translation of debulker 204) to remove portions of the lesion P. It is noted that these steps have been described in a generally sequential matter for the optimum cases, and it should be kept in mind that these steps can be performed in any order as deemed appropriate by the operator for the circumstances at hand.

While the invention has been described in terms of particular variations and illustrative figures, those of ordinary skill in the art will recognize that the invention is not limited to the variations or figures described. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well.

What is claimed is:

1. A method of debulking lesions disposed inside a body vessel, the method comprising the steps of:
   inserting a catheter into the body vessel proximate the lesions, the catheter including:
   an outer sheath extending along a longitudinal axis, the outer sheath surrounding a portion of a first tubular member, the first tubular member surrounding at least a portion of a second tubular member, the second tubular member disposed around a portion of a third tubular member, the third tubular member disposed around a portion of an axially moveable fourth tubular member;
   a first balloon coupled to the first tubular member;
   a rotary debulker being coupled to the second tubular member so that the rotary debulker is rotatable about the longitudinal axis by rotational motion of the second tubular member about the longitudinal axis; and
   a second balloon coupled to both the third tubular member and the axially moveable fourth tubular member such that the second balloon is disposed inside the third tubular member and wherein a distal end of the axially moveable fourth tubular member is configured to be extendable beyond a distal end of the third tubular member;
   inflating the first balloon for abutment against the internal surface of the body vessel;
   rotating the rotary debulker to remove portions of the lesion at a first location; axially advancing the catheter into the lesion at a second location spaced from the first location; and
   pulling the fourth tubular member along the longitudinal axis in a distal direction by inflation of the second balloon so that a tip of the fourth tubular member extends into a plaque material occluding the vessel.

2. The method of claim 1, further comprising rotating the rotary debulker about a longitudinal axis to remove portions of the lesion.

* * * * *